United States Patent [19]
Karsten

[11] Patent Number: 6,136,394
[45] Date of Patent: Oct. 24, 2000

[54] TUBE COMPRISING AT LEAST THREE LAYERS

[75] Inventor: Petrus J. A. Karsten, Enkhuizen, Netherlands

[73] Assignee: Solvay (Societe Anonyme), Brussels, Belgium

[21] Appl. No.: 09/021,309

[22] Filed: Feb. 10, 1998

[30] Foreign Application Priority Data

Feb. 11, 1997 [BE] Belgium ................................ 09700126

[51] Int. Cl.⁷ .......................... A61M 25/10; A61M 25/16; B29D 22/00; B29D 22/02

[52] U.S. Cl. .................... 428/35.7; 428/36.7; 428/36.91; 428/475.2; 604/523

[58] Field of Search ................................ 428/35.7, 36.91, 428/475.2; 604/262, 264, 523

[56] References Cited

U.S. PATENT DOCUMENTS

| | | | |
|---|---|---|---|
| 4,349,469 | 9/1982 | Davis et al. | 524/765 |
| 4,480,086 | 10/1984 | O'Neill | 528/295.3 |
| 5,069,955 | 12/1991 | Tse et al. | 428/213 |
| 5,532,053 | 7/1996 | Mueller | 428/287 |
| 5,645,904 | 7/1997 | Woo et al. | 428/35.7 |
| 5,803,130 | 9/1998 | Robben et al. | 138/137 |

*Primary Examiner*—Ellis Robinson
*Assistant Examiner*—Sandra M. Nolan
*Attorney, Agent, or Firm*—Venable

[57] ABSTRACT

Tube comprising:

(a) an inner layer essentially consisting of a copolyester obtained from at least one poly(alkylene oxide) glycol, 1,4-cyclohexanedicarboxylic acid and 1,4-cyclohexanedimethanol;

(b) an interlayer essentially consisting of an ethylene-vinyl acetate copolymer and/or of a copolymer containing at least one polyamide block and at least one poly(alkylene oxide) block; and (c) an outer layer essentially consisting of a copolyester obtained from at least one poly(alkylene oxide) glycol, 1,4-cyclohexanedicarboxylic acid and 1,4-cyclohexanedimethanol.

This tube may advantageously be used in medical applications.

10 Claims, No Drawings

TUBE COMPRISING AT LEAST THREE LAYERS

BACKGROUND OF THE INVENTION

The present invention relates to a multilayer tube which can in particular be advantageously used in medical applications whose requirements are very demanding.

Several specific polymers have already been proposed in order to satisfy these requirements. Thus, for example, it has already been proposed to use copolyesterethers manufactured from poly(tetramethylene oxide) glycol, 1,4-cyclohexanedicarboxylic acid and 1,4-cyclohexanedimethanol. The manufacture of such copolymers (called hereinafter "PCCE") is, for example, described in U.S. Pat. No. 4,349,469.

The requirements imposed on tubes for medical use are, in particular, flexibility, (medical-grade) nontoxicity, transparency and high-frequency (HF) weldability requirements. The manufacture of such tubes consequently poses very specific problems, which means that polymers suitable for manufacturing films, for example, are not necessarily suitable for manufacturing tubes.

Thus, PCCEs which are suitable for manufacturing films are ill-suited for manufacturing tubes because of their rapid crystallization, which has a negative effect on the transparency and on the flexibility. Certainly, rapid (quench) cooling may help to alleviate these problems, but this solution is effective only for extremely small thicknesses, for example, thicknesses of less than 200 $\mu$m. A quench would thus constitute a satisfactory solution only in the manufacture of extremely thin tubes, but is not by itself sufficient when the manufacture of tubes for medical use is envisaged, which generally have a thickness of 500 $\mu$m. Furthermore, PCCEs are relatively not very polar and therefore ill-suited to HF welding.

SUMMARY OF THE INVENTION

The present invention aims to remedy these problems and to provide a tube which is flexible, transparent, HF weldable and nontoxic.

DETAILED DESCRIPTION OF THE INVENTION

More specifically, the present invention relates to a tube comprising:

(a) an inner layer essentially consisting of a copolyester obtained from at least one poly(alkylene oxide) glycol, 1,4-cyclohexanedicarboxylic acid and 1,4-cyclohexanedimethanol;

(b) an interlayer essentially consisting of an ethylene-vinyl acetate copolymer and/or of a copolymer containing at least one polyamide block and at least one poly(alkylene oxide) block; and (c) an outer layer essentially consisting of a copolyester obtained from at least one poly(alkylene oxide) glycol, 1,4-cyclohexanedicarboxylic acid and 1,4-cyclohexanedimethanol.

Advantageously, the inner layer (a) has a thickness not exceeding 300 $\mu$m and preferably not exceeding 200 $\mu$m, which allows it to remain satisfactorily flexible and satisfactorily transparent. Its thickness is, more-over, generally at least 50 $\mu$m.

The polymer making up layer (a) is a copolyester containing one or more polyether-type blocks (poly(alkylene oxide)) which may be obtained by the prior polymerization of compounds of the alkylene glycol type (for example tetramethylene glycol) or of the cyclic ether type (for example, tetrahydrofurane) and which are then copolymerized with the abovementioned constituents in the form of poly(alkylene oxide) glycols. The poly(alkylene oxide) of the copolyester of layer (a) may be of any known type, for example poly(propylene oxide) or poly(tetramethylene oxide). Preferably, the poly(alkylene oxide) of the copolyester of layer (a) is poly(tetramethylene oxide). Apart from the abovementioned three initial reactants (poly(alkylene oxide) glycol, 1,4-cyclohexanedicarboxylic acid and 1,4-cyclohexanedimethanol), the copolyester of layer (a) may also be synthesized in the presence of a moderate amount of one or more branching agents such as, for example, triacids or trialcohols, allowing branched polymer chains to be obtained. Layer (a) may, of course, contain several copolyesters of this type.

The thickness of the interlayer (b) may be adjusted depending on the specific requirements of mechanical strength, flexibility, transparency, weldability, etc. of the tube. Good results have been obtained by giving layer (b) a thickness of 100 to 600 $\mu$m. However, if layer (b) consists of ethylene-vinyl acetate copolymer (EVA), it is preferable to limit its thickness to 300 $\mu$m, this being so as to avoid any problems with regard to steam sterilization. It will be noted that the choice of polymer making up the inner layer is nontrivial; thus, PCCE/PVC/PCCE triple-layer tube extrusion trials have resulted in severe degradation of the PVC making up the interlayer.

When layer (b) consists of ethylene-vinyl acetate copolymer, it is advantageous for the vinyl acetate content of the latter to be about 10 to 40% by weight.

When layer (b) consists of a copolymer (commonly called "polyester block amide" or "PEBA" for short) containing at least one polyamide block and at least one poly(alkylene oxide) block, it is advantageous for the latter to be a poly(tetramethylene oxide) block. In this case, good results have moreover been obtained by specifically using a copolymer containing at least one nylon-12 block and at least one poly(alkylene oxide) block. Layer (b) may, of course, contain several polymers of these types.

The thickness of layer (c) is preferably 50 to 400 $\mu$m. Since the outer layer is easier to cool than the inner layer, this therefore allows greater thicknesses. According to an advantageous variant, the poly(alkylene oxide) of the copolyester of layer (c) is poly(tetramethylene oxide). Layer (c) may, of course, contain several polymers of the type described above.

Apart from the abovedefined polymers, layers (a), (b) and/or (c) may also contain moderate amounts of one or more of the usual additives, such as antioxidants, stabilizers, pigments etc., as long as this does not impair the final properties of the tube.

Apart from layers (a), (b) and (c), the tube may also include one or more other layers, as long as these do not impair the desired properties. In particular, in order to optimize the mutual adhesion of the various abovementioned layers, one or more adhesive layers may be interposed between them. With a view to dispensing with such adhesives, an advantageous variant consists [lacuna] that layer (b) essentially consists of a copolymer containing at least one polyamide block and at least one poly(alkylene oxide) block and in that the same poly(alkylene oxide) is used in the polymers making up layers (a), (b) and (c).

Very good results have been obtained with tubes in which the 3 layers (a), (b) and (c) have the following thicknesses: (a) from 50 to 300 $\mu$m, (b) from 100 to 600 $\mu$m and (c) from 50 to 400 $\mu$m.

The tube of the invention is advantageously manufactured by a coextrusion process. Preferably, immediately after the tube has been extruded it is subjected to rapid (quench) cooling for the purpose of improving its flexibility and transparency.

The tube of the invention may, of course, be used in applications other than medical applications.

However, it is particularly applicable to uses in the medical field. Its good HF weldability allows it to be easily welded to flexible containers such as bags intended to contain blood or other liquids for medical use. For this purpose, the present invention also relates to a device for dispensing products for medical use—in particular, a blood bag—comprising at least one thermoplastic-based flexible bag to which at least one tube as described above is welded. The welding is advantageously carried out by HF welding. The invention also relates to a process for manufacturing such a dispensing device, involving an HF welding step.

What is claimed is:

1. A tube comprising:
   (a) an inner layer consisting essentially of a copolyester obtained from at least one of poly (alkylene oxide) glycol, 1,4-cyclohexanedicarboxylic acid and 1,4-cyclohexanedimethanol;
   (b) an interlayer consisting essentially of at least one of an ethylene-vinyl acetate copolymer and a polyester block amide containing at least one polyamide block and at least one poly(alkylene oxide) glycol block; and
   (c) an outer layer consisting essentially of a copolyester of poly(alkylene oxide) glycol, 1,4-cyclohexanedicarboxylic acid and 1,4-cyclohexanedimethanol;
   said layers being co-extruded into a flexible tube suitable for high-frequency welding;
and said tube having a thickness of at least about 200 microns.

2. The tube according to claim 1, in which the poly (alkylene oxide) of the copolyester of layer (a) is poly (tetramethylene oxide).

3. The tube according to claim 1, in which layer (b) essentially consists of a copolymer containing at least one polyamide block and at least one poly(tetramethylene oxide) block.

4. The tube according to claim 1, in which layer (b) essentially consists of a copolymer containing at least one nylon-12 block and at least one poly(alkylene oxide) block.

5. The tube according to claim 1, in which the poly (alkylene oxide) of the copolyester of layer (c) is poly (tetramethylene oxide).

6. The tube according to claim 1, in which layer (b) essentially consists of a copolymer containing at least one polyamide block and at least one poly(alkylene oxide) block and in which the same poly(alkylene oxide) is used in the polymers making up layers (a), (b) and (c).

7. The tube according to claim 1, in which layer (a) has a thickness of 50 to 300 $\mu$m.

8. The tube according to claim 1, in which layer (b) has a thickness of 100 to 600 $\mu$m.

9. The tube according to claim 1, in which layer (c) has a thickness of 50 to 400 $\mu$m.

10. A medical device comprising:
    at least one thermoplastic-based flexible bag and at least one tube, said at least one tube having:
        an inner layer consisting essentially of a copolyester obtained from at least one of poly(alkylene oxide) glycol, 1,4-cyclohexanedicarboxylic acid and 1,4-cyclohexanedimethanol;
        an interlayer consisting essentially of at least one of an ethylene-vinyl acetate copolymer and a polyester amide block containing at least one polyamide block and at least one poly(alkylene oxide) glycol block; and
        an outer layer consisting essentially of a copolyester of poly(alkylne oxide) glycol, 1,4-cyclohexanedicarboxylic acid and 1,4-cyclohexanedimethanol;
    wherein said at least one tube is formed by coextrusion, said tube having a thickness of at least 200 microns, and said tube being high-frequency welded to said at least one flexible bag.

* * * * *